United States Patent [19]

Choksi

[11] Patent Number: 5,176,415
[45] Date of Patent: Jan. 5, 1993

[54] TAPER FITTING WITH PROTECTIVE SKIRT

[76] Inventor: Pradip V. Choksi, 10935 Yolanda Ave., Northridge, Calif. 91326

[21] Appl. No.: 568,090

[22] Filed: Aug. 16, 1990

[51] Int. Cl.⁵ .............................................. F16L 19/00
[52] U.S. Cl. ..................................... 285/331; 285/33; 285/332.1; 285/330
[58] Field of Search ...................... 285/3, 32, 33, 330, 285/332.1, 332.2, 331

[56] References Cited

U.S. PATENT DOCUMENTS

| | | | |
|---|---|---|---|
| 3,427,707 | 12/1965 | Nowosadko | 285/332.1 |
| 3,633,586 | 1/1972 | Sheridan . | |
| 3,752,510 | 2/1973 | Windischman et al. . | |
| 3,902,489 | 9/1975 | Carter | 285/3 X |
| 3,986,508 | 10/1976 | Barrington | 285/3 X |
| 4,046,479 | 2/1977 | Paley . | |
| 4,187,846 | 2/1980 | Lolachi et al. . | |
| 4,201,208 | 5/1980 | Cambio | 285/3 X |
| 4,201,406 | 5/1980 | Dennehey et al. | 285/3 |
| 4,254,773 | 3/1981 | Waldbillig . | |
| 4,266,815 | 5/1981 | Cross . | |
| 4,296,949 | 10/1981 | Muetterties et al. . | |
| 4,326,569 | 4/1982 | Vaillancourt . | |
| 4,369,781 | 1/1983 | Gilson et al. . | |
| 4,452,473 | 6/1984 | Ruschke . | |
| 4,508,367 | 4/1985 | Oreopoulos et al. | 285/3 |
| 4,511,359 | 4/1985 | Vaillancourt | 285/3 X |
| 4,538,836 | 9/1985 | Krutten . | |
| 4,566,480 | 1/1986 | Parham . | |
| 4,607,868 | 8/1986 | Harvey et al. . | |
| 4,610,969 | 9/1986 | Wolf-Mooij | 285/3 X |
| 4,634,027 | 1/1987 | Kanarvogel . | |
| 4,639,019 | 1/1987 | Mittleman . | |
| 4,649,904 | 3/1987 | Krauter et al. . | |
| 4,653,539 | 3/1987 | Bell . | |
| 4,676,530 | 6/1987 | Nordgren et al. . | |
| 4,693,710 | 9/1987 | McCool . | |
| 4,704,177 | 11/1987 | Vaillancourt . | |
| 4,735,441 | 4/1988 | Stephen . | |
| 4,737,334 | 4/1988 | Folding et al. . | |
| 4,801,296 | 1/1989 | Vaillancourt . | |
| 4,919,167 | 4/1990 | Manska . | |
| 4,929,235 | 5/1990 | Merry et al. . | |
| 4,932,114 | 6/1990 | Morse et al. . | |

*Primary Examiner*—Randolph A. Reese
*Assistant Examiner*—Timothy Aberle
*Attorney, Agent, or Firm*—Stetina and Brunda

[57] ABSTRACT

An apparatus for quickly disconnecting two tubular flow lines comprising first and second units including first and second tubular members which have mutually tapering interengagement surfaces, and end terminals, the members respectively associated with the two flow lines and the members being axially interfittable; the first and second units including first and second protectors respectively associated with and extending about the end terminals, the protectors positioned to radially and axially overlap when the members are brought into interfitting interengagement at the tapering surfaces.

5 Claims, 2 Drawing Sheets

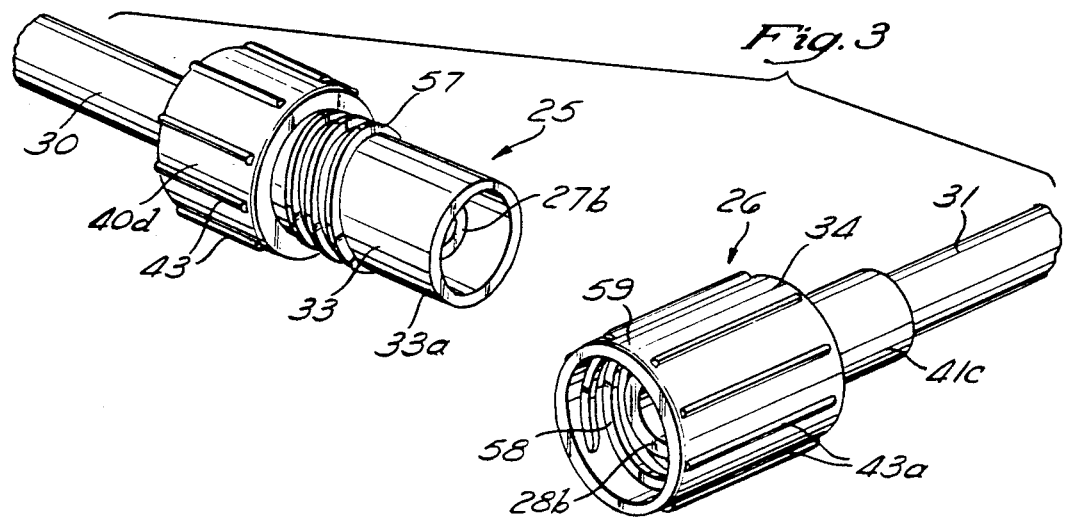
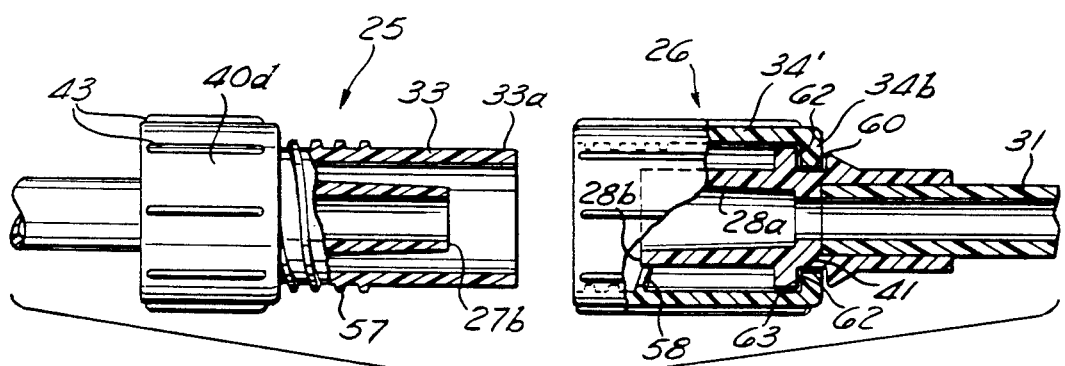
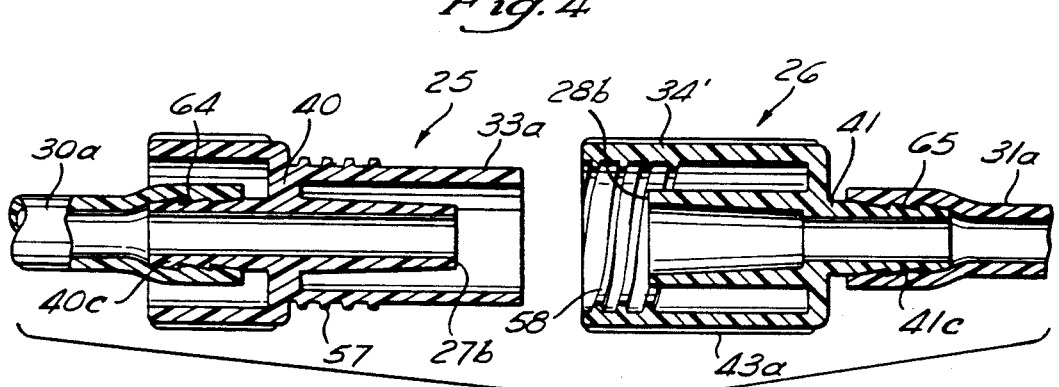

TAPER FITTING WITH PROTECTIVE SKIRT

BACKGROUND OF THE INVENTION

This invention relates generally to fittings used in connecting tubings as used in medical devices, and more particularly concerns protecting such tubing connections against contamination.

In hospitals, taper fittings are commonly used to connect tubings carrying intravenous fluids, blood and medications The most commonly used taper fitting is the luer. This is a small diameter fitting with a through hole of about 1/16 inch . The male luer fitting is often provided with a skirt with internal threads. The matching female luer has locking ears or external threads to give a secure connection. FIG. 1 shows typical male and female luers with locking threads. Note that the female luer has no skirt and the tip of the male luer extends beyond the threaded skirt.

When a luer fitting is disconnected, fluid such as blood that is flowing through the tubing can be easily touched by the person disconnecting the fittings. This creates two problems. First, the sterility of the system is compromised because any touching of the tips of luer fittings introduces contaminants into the system. Secondly, the person comes in contact with the body fluids that may be infectious. With recent concerns about AIDS and other infectious diseases, this is a serious problem.

There is urgent need for simple, effective means to protect such fittings and tubing connections against contamination.

SUMMARY OF THE INVENTION

It is a major object of the invention to provide improved fitting or connection apparatus meeting the above need. Basically, the improved apparatus is characterized as enabling quick connection and/or disconnection of two tubular flow lines, as for example plastic tubing as used in medical or hospital environments, and includes:

a) first and second units including first and second tubular members which have mutually tapering interengagement surfaces, and end terminals, the members respectively associated with the two flow lines and the members being axially interfittable, b) the first and second units including first and second protectors respectively associated with and extending about the end terminals, the protectors positioned to radially and axially overlap when the members are brought into interfitting interengagement at the tapering surfaces.

It is another object to provide first and second units include first and second tubular body structures, the first body structure integral with the first tubular member and first protector, and the second body structure integral with the second tubular member and second protector.

Yet another object is to provide protectors that comprise skirts extending in co-axial and concentric relation when the members are brought interfitting interengagement. Such skirts may typically be tubular, each skirt extending beyond its associated member end terminal, whereby a user's fingers cannot gain easy access to the tubular members that typically define a luer-type connection. As will be seen, the members and connections typically consist of molded plastic material.

Additional objects include provision of interengabeable threads on the first and second units to retain them in interengaged relation when the engagement surfaces on the tubular members are brought into interengagement; and provision for rotation of one protector on one of the body structures, and about a common axis defined by the one structure and one unit.

Advantages and unique features of the invention include:

1. Eliminates touch contamination of aseptic fluid path.
2. Eliminates the risk of health care worker coming in contact with infectious fluids.
3. Maintains currently used connect/disconnect techniques for taper fittings.
4. Spinning nut provides twist-free connection and disconnection.
5. Clear material permits visualization of the tapered interface.
6. Ribs provide firm grip for connection and disconnection.
7. Fittings designed for either adhesive bond or barbed gripping of the tubing.

These and other objects and advantages of the invention, as well as the details of an illustrative embodiment, will be more fully understood from the following specification and drawings, in which:

DRAWING DESCRIPTION

FIG. 3 is a perspective view showing the FIG. 2 elements; and

FIGS. 4 and 5 show modification of the FIG. 2 system.

DETAILED DESCRIPTION

Figure 1:
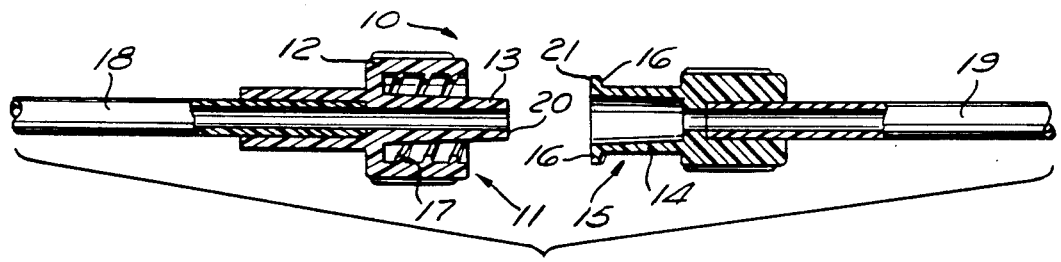
FIG. 1 is an elevation, taken in section, showing a known connection.

In FIG. 1, the fitting 10 shown includes male luer 11 with a skirt 12, and a stem 13. The latter is received in a receptacle 14 of female luer 15 having ears 16, that engage threads 17 in skirt 12.

Flexible tubings appear at 18 and 19. Unprotected surfaces 20 and 21 may become moistened with body fluid that may be contaminated. The doctor or nurse, or other hospital attendant, who handles the fitting 10 (connecting or disconnecting same) can easily touch surfaces 20 and 21, thereby becoming exposed to such contamination.

The improved device of the present invention basically includes first and second units including first and second tubular members which have mutually tapering interengagement surfaces, and end terminals, the members respectively associated with the two flow lines and the members being axially interfittable.

In the example, the connector includes first and second units 25 and 26. Male unit 25 includes a first tubular member 27 projecting rightwardly, and typically having an external, elongated and tapered engagement surface 27a and an end terminal 27b. Female unit 26 includes a second tubular member 28, projecting leftwardly and typically having an internal, elongated and tapered, engagement surface 28a with an end terminal at 28b. Such tapers are matching and sufficiently shallow (as in a luer fitting) that surface interengagement friction tends to hold them together; however, they need not be so tapered. The members 27 and 28 are respectively associated with the two tubular flow lines 30 and 31, which may be flexible and transparent.

The first and second units 25 and 26 also include first and second protectors respectively associated with and extending about the end terminals, the protectors positioned to radially and axially overlap when the members are brought into interfitting interengagement at the tapering surfaces.

Figure 2:
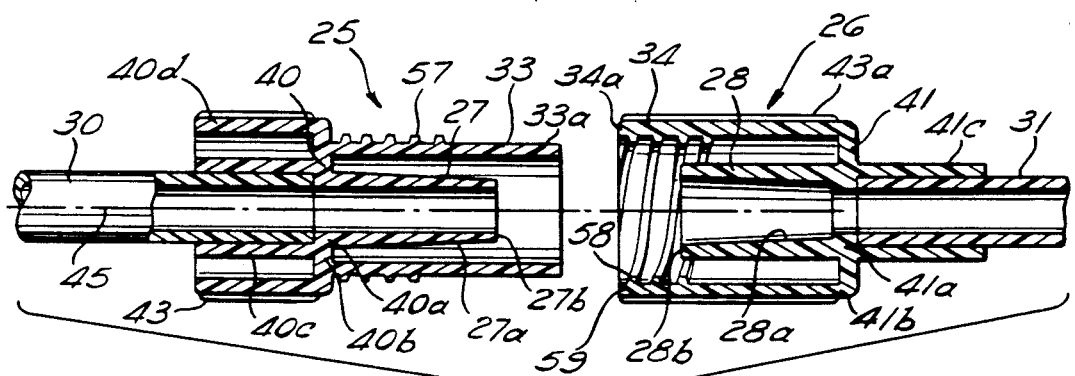
FIG. 2 is a view like Fig but showing a connection or fitting embodying the invention.

In the example, the protectors take the form of skirts 33 and 34 respectively spaced radially outwardly of the end terminals 27b and 28b, (and also the surfaces 27a and 28a); and they typically extend axially beyond those end terminals, as indicated by end extents 33a and 34a of the skirts 33 and 34. It is clear from FIG. 2., showing the units 25 and 26 in disconnected condition, that the fingers of the doctor, nurse or medical attendant are protected by the skirts from inadvertent touching of the end terminals 27b and 28b (which may be moistened or otherwise contaminated by fluid, for example blood or intravenous fluid flowing to or from the patient). The tubular members 27 and 28, as well as the skirts 33 and 34, may consist of molded plastic material that may be transparent, for viewing of flow therethrough.

Figure 2A:
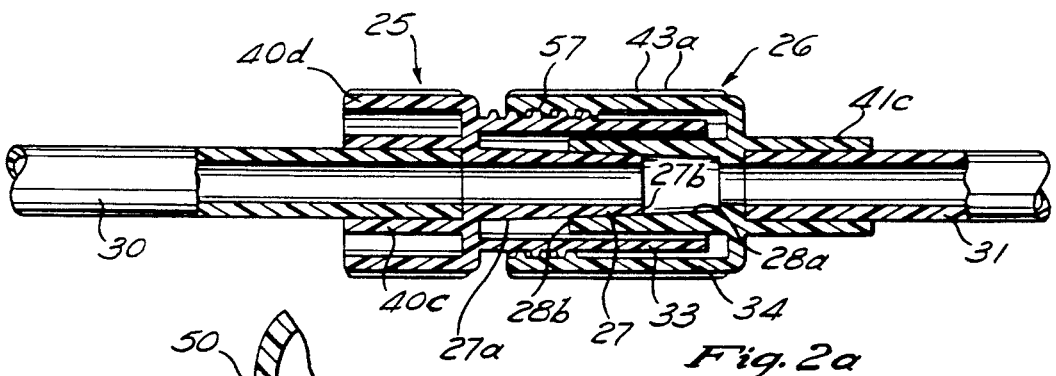
FIG. 2a shows the FIG. 2 members in made-up condition.

When the units 25 and 26 are interconnected, the skirts are seen in FIG. 2a to extend in coaxial and concentric relation. In this regard, the two units typically may include first and second body structures, the first body structure integral with the first tubular member and first protector, and the second body structure integral with the second tubular member and second protector.

Figure 2B:
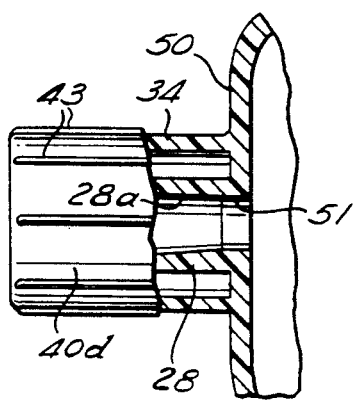
FIG. 2b shows one unit integral with a bottle.

In the example, a first tubular body structure 40 merges with the leftward end of the member 27 at 40a, and with the leftward end of the skirt 33 at 40b; and a second body structure 41 merges with the rightward end of the member 29 at 41a, and with the rightward end of the skirt 34 at 41b. Structure 40 also includes leftwardly projecting tubular extents 40c and 40d. Extent 40c is sized to telescopically interfit the end of flexible flow line 30; and 40d is spaced radially outwardly of 40c and provides outer grip edges 43, such as ribs, spaced about the axis 45 for manual grasping, as during connection and disconnection of the units 25 and 26. Ribs 43a are also provided on skirt 34. Structure 41 also includes rightwardly projecting tubular extent 41c sized to telescopically interfit the end of flexible flow line 31, as shown, and to be bonded thereto. Either of the units 25 and 26 can be integral with a bottle 50, as is shown in FIG. 2b, wherein body structure 41 merges with a bottle wall, the tubular extent 51 to be considered a "flow line". The body structures 40 and 41 may also consist of molded plastic material, which is transparent for viewing.

The units may also incorporate interengageable threads to retain them in interengaged relation when said engagement surfaces on the tubular members are brought into interengagement. See for example external screw threading 57 on the protector 40, and also on the base of skirt 33; and the internal threading 58 on leftward extent 59 of skirt 34. FIG. 2b shows the made-up condition of the units.

One of the protectors may be mounted for rotation on one of the body structures, and about a common axis defined by the one structure and one unit. See in this regard FIG. 4 showing skirt 34' having an internal rightward end portion, or annular flange 34b, fitting in an annular groove 60 in body structure 41, to allow relative annular rotation of the protector and body structure, as during make-up. Tightening during make-up establishes an annular seal at surfaces 62 and 63, as shown.

FIG. 5 shows barbed interfits, as at 64, between tubing flow line 30a and tubular extent 40c of the body 40; and also at 65 between tubing flow line 31a and tubular extent 41c of the body 41.

TYPICAL APPLICATIONS OF THE INVENTION

1. Intravenous Therapy. Connection of intravenous catheter to intravenous set. Connection of extension tubing to intravenous set or catheter.
2. Blood Infusion. Connection of blood infusion set to catheter.
3. Wound Drainage. Connection of wound drain tube to evacuation container.
4. Autotransfusion. Connection of drain tube to collection container.
5. Chest Drainage. Connection of chest drainage tube to catheter or collection container.
6. Urology. Connection of Foley catheter to drainage tube, and connection of urine bag emptying port to other collection receptacles.
7. Suctioning. Connecting suction catheters to suction line.
8. Other Applications. Several other applications not specifically mentioned here are possible for this invention.

I claim:

1. A shrouded tubing interface for quickly connecting, disconnecting and avoiding contamination of first and second fluid flow lines, comprising:

a first connector having a first tubular member defining an open flow path with a first fluid flow line, said first tubular member having an outer annular surface and defining a first end terminal, a first extension for telescopically receiving said first fluid flow line, and a third extension extending radially outward of and axially overlapping said first extension, said first connector further including a first tubular skirt extending radially outward of and axially beyond said first end terminal to form a physical barrier to prevent inadvertent contact with said first end terminal so as to prevent contamination thereof;

a second connector having a second tubular member defining an open flow path with a second fluid flow line, said second tubular member having an aperture extending axially therethrough and defining a second end terminal and a second extension for telescopically receiving said second fluid flow line, said second connector further including a second tubular skirt extending radially outward of and axially beyond said second end terminal to form a physical barrier to prevent inadvertent contact with said second end terminal so as to prevent contamination thereof;

male threads formed upon a portion of said first tubular skirt; and female threads disposed within a portion of said second tubular skirt;

said first and second connectors being releasably connectable via the receipt of said male threads of said first tubular skirt into the female threads of said second tubular skirt, said tubular skirts extending in co-axial and concentric relation and said outer surface of said first tubular member being slidably receivable into said aperture when said first connector is connected to said second connector.

2. The device of claim 1 wherein said second tubular skirt and said third extension include outer surfaces having a plurality of grip edges formed thereon, said grip edges being adapted to aid in the connection of said first connector to said second connector.

3. The device of claim 1 wherein the outer surface of said first tubular member and the aperture of said second tubular member have mutually tapered configurations.

4. The device of claim 1 wherein said second tubular skirt is rotatably connected to said second connector for allowing said female threads to be threadably engaged to said male threads without rotating said second tubular member.

5. The device of claim 1 wherein said first extension includes an outer surface having a barbed configuration for being frictionally retained within said first fluid flow line and said second extension includes an outer surface having a barbed configuration for being frictionally retained within said second fluid flow line.

* * * * *